United States Patent
Rockrohr (10) Patent No.: US 8,968,188 B2
(45) Date of Patent: Mar. 3, 2015

(54) EXPANDABLE SEGMENTED AND SECTIONED ACCESS ASSEMBLY

(75) Inventor: Brian Rockrohr, Waterbury, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/224,356

(22) Filed: Sep. 2, 2011

(65) Prior Publication Data

US 2012/0130179 A1    May 24, 2012

Related U.S. Application Data (60) Provisional application No. 61/416,771, filed on Nov. 24, 2010.

(51) Int. Cl.
| | |
|---|---|
| A61B 1/32 | (2006.01) |
| A61B 17/02 | (2006.01) |
| A61B 17/34 | (2006.01) |
| A61B 17/00 | (2006.01) |

(52) U.S. Cl.
CPC ......... *A61B 17/3423* (2013.01); *A61B 17/3431* (2013.01); *A61B 2017/00557* (2013.01); *A61B 2017/3445* (2013.01); *A61B 2017/3486* (2013.01)
USPC ............................ 600/205; 600/207; 600/208

(58) Field of Classification Search
USPC .......... 600/201–208, 210, 215, 224; 606/191, 606/192, 193–197, 198, 199
See application file for complete search history.

(56) References Cited

U.S. PATENT DOCUMENTS

| | | | |
|---|---|---|---|
| 4,984,564 A * | 1/1991 | Yuen ............................. | 600/207 |
| 5,361,752 A | 11/1994 | Moll et al. | |
| 5,520,609 A * | 5/1996 | Moll et al. .................... | 600/204 |
| 5,823,945 A | 10/1998 | Moll et al. | |
| 5,906,577 A * | 5/1999 | Beane et al. .................. | 600/207 |
| 5,951,514 A | 9/1999 | Sahota | |
| 6,033,428 A | 3/2000 | Sardella | |
| 6,846,287 B2 | 1/2005 | Bonadio et al. | |
| 6,846,296 B1 | 1/2005 | Milbocker et al. | |
| 6,908,430 B2 | 6/2005 | Caldwell et al. | |

(Continued)

FOREIGN PATENT DOCUMENTS

| | | |
|---|---|---|
| EP | 2 044 889 | 4/2009 |
| EP | 2196161 A1 | 6/2010 |

(Continued)

OTHER PUBLICATIONS

EP Search Report for corresponding EP11250801, date of mailing Jun. 15, 2012 (9 pages).

(Continued)

*Primary Examiner* — Michael T Schaper
*Assistant Examiner* — Tracy Kamikawa (57) ABSTRACT

An improved access assembly is provided. The access assembly includes a tubular member having a proximal end and a distal end, the tubular member including at least one section extending at least a portion of a length therein. The access assembly further includes a first ring including a plurality of first segments and secured at the proximal end of the tubular member and a second ring including a plurality of second segments and secured at the distal end of the tubular member. At least two segments of the first plurality of segments are independently expandable. At least two sections of the plurality of sections are independently expandable.

16 Claims, 8 Drawing Sheets

(56) References Cited

U.S. PATENT DOCUMENTS

| | | |
|---|---|---|
| 6,939,296 B2 | 9/2005 | Ewers et al. |
| 6,974,441 B2 | 12/2005 | Ravo |
| 7,214,185 B1 | 5/2007 | Rosney et al. |
| 7,481,765 B2 | 1/2009 | Ewers et al. |
| 7,850,600 B1 | 12/2010 | Piskun |
| 8,241,209 B2 * | 8/2012 | Shelton et al. ............... 600/207 |
| 2001/0020150 A1 | 9/2001 | Ravo |
| 2003/0014076 A1 | 1/2003 | Mollenauer et al. |
| 2003/0181939 A1 | 9/2003 | Bonutti |
| 2004/0092795 A1 | 5/2004 | Bonadio et al. |
| 2004/0267096 A1 | 12/2004 | Caldwell et al. |
| 2005/0192531 A1 | 9/2005 | Birk |
| 2006/0089596 A1 | 4/2006 | Ravo |
| 2007/0085232 A1 | 4/2007 | Brustad et al. |
| 2008/0081951 A1 | 4/2008 | Frasier et al. |
| 2008/0091080 A1 * | 4/2008 | Leahy ........................... 600/207 |
| 2009/0118587 A1 | 5/2009 | Voegele et al. |
| 2009/0221966 A1 | 9/2009 | Richard |
| 2010/0069859 A1 | 3/2010 | Weig |
| 2010/0312065 A1 | 12/2010 | Shelton, IV et al. |

FOREIGN PATENT DOCUMENTS

| | | |
|---|---|---|
| EP | 2 289 438 | 3/2011 |
| EP | 2 343 019 | 7/2011 |
| WO | WO 00/54675 | 9/2000 |
| WO | WO 2004/075730 A2 | 9/2004 |
| WO | WO2004/093699 A1 | 11/2004 |

OTHER PUBLICATIONS

European Search Report from EP Application No. EP 12 15 2164 mailed Apr. 19, 2012.

European Search Report from EP Application No. EP 12 15 2128 mailed Apr. 20, 2012.

* cited by examiner

EXPANDABLE SEGMENTED AND SECTIONED ACCESS ASSEMBLY

CROSS REFERENCE TO RELATED APPLICATIONS

The present application claims the benefit of and priority to U.S. Provisional Patent Application Ser. No. 61/416,771 filed on Nov. 24, 2010, the entire contents of which are incorporated herein by reference.

BACKGROUND

1. Technical Field

The present disclosure relates to an apparatus and method for accessing a body cavity. More particularly, the present disclosure relates to an expandable segmented and/or sectioned access assembly.

2. Background of Related Art

Access assemblies configured for reception through an incision into an abdominal cavity are known, as are methods of inserting the access assemblies therethrough. Traditional access assemblies include a rigid cannula that is received through the tissue of the body wall into the body cavity. Endoscopic, laparoscopic and other suitable instruments may then be directed through a housing on the proximal end of the cannula to access the body cavity in a sealing manner.

Compressible assemblies configured for accessing a body cavity and permitting reception of instruments therethrough in a sealing manner are also known. Such compressible assemblies are composed of silicone, thermoplastic elastomers (TPE), rubber, foam, gel and other compressible materials and are configured to be compressed to facilitate insertion into an incision. Typically, such assemblies are deformed by a surgeon using his/her fingers or with the assistance of a grasping device, i.e., forceps. Compression of the assembly reduces the profile of the assembly, thereby facilitating reception of the assembly into the incision. Upon release of the compressive force, the compressed assembly returns to an uncompressed configuration. In the uncompressed configuration, the access assembly seals the incision into the body cavity. The assembly may have one or more access ports for receiving instruments therethrough and may optionally be configured for connection with a source of insufflation gas.

Excessive handling of the compressible access assemblies during placement of the assembly through an incision may compromise or otherwise negatively affect the integrity of the assembly. For example, any coating on the assembly may be rubbed off during handling, or excessive force, oversized/undersized fingers and/or sharp grasping instruments may tear the material comprising the assembly.

Therefore, it would be beneficial to have an access assembly configured to be inserted through tissue without excessive handling and/or without the need for an insertion device.

SUMMARY

Accordingly, an expandable access assembly is provided. The access assembly includes a tubular member having a proximal end and a distal end, the tubular member including one or more sections extending at least a portion of a length therein. The access assembly further includes a first ring including a plurality of first segments and secured at the proximal end of the tubular member and a second ring including a plurality of second segments and secured at the distal end of the tubular member. The plurality of first segments, the plurality of second segments, and the one or more sections are independently or jointly expandable with respect to each other.

In one embodiment, the first ring is configured to be received external of tissue and the second ring is configured to be received within a body cavity.

The tubular member is configured to be tapered in a first configuration to facilitate insertion through tissue and is configured to define a substantially hour-glass shape in a second configuration.

The first and second rings are configured for operable connection with a fluid source such that the plurality of first and second segments are independently or jointly expanded or contracted. Fluid sources include gas ($CO_2$) or liquids (saline).

Each of the one or more sections of the tubular member is configured for operable connection with a fluid source. Each of the plurality of first segments are configured to be selectively expanded/contracted to different sizes with respect to each other and each of the plurality of second segments are configured to be selectively expanded/contracted to different sizes with respect to each other. Each of the one or more sections of the tubular member is configured to be selectively expanded/contracted to different sizes with respect to each other.

In yet another embodiment, a first pressure is applied to the plurality of first segments to expand the first segments to a first size and a second pressure is applied to the plurality of second segments to expand the second segments to a second size, the first size being larger than the second size.

Additionally, each of the one or more sections includes one or more channels for receiving one or more surgical instruments. The one or more channels of each of the one or more sections is sealed from losing insufflation gas when a subject inserts and removes surgical instruments from the one or more channels.

Also provided is a method of accessing a body cavity. The method includes the step of providing a tubular member having a proximal end and a distal end, the tubular member including one or more sections extending at least a portion of a length therein. The method further includes providing a first ring including a plurality of first segments and secured at the proximal end of the tubular member and providing a second ring including a plurality of second segments and secured at the distal end of the tubular member. The method also includes independently or jointly expanding with respect to each other the plurality of first segments, the plurality of second segments, and the one or more sections.

Also provided is a method of accessing a body cavity. The method includes the steps of providing a tubular member, a first ring having a plurality of first segments, and a second ring having a plurality of second segments, the tubular member being configured to be tapered in a first configuration to facilitate insertion through tissue and being configured to define a substantially hour-glass shape in a second configuration; inserting the tapered access assembly through tissue; adjusting the access assembly in the second configuration; and independently or jointly expanding with respect to each other the plurality of first segments, the plurality of second segments, and the one or more sections.

In addition, while certain aspects of this disclosure are described as relating to laparoscopic surgery via the abdominal wall, it should be understood that the present invention is equally relevant to, and may be employed in connection with, other types of surgery such as incision-less surgery, whereby access to a body cavity is provided via a natural orifice such as the vagina, anus, mouth, ear, nasal passage, etc.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Embodiments of the presently disclosed apparatus will now be described in detail with reference to the drawings, in which like reference numerals designate identical or corresponding elements in each of the several views. As used herein, the term "distal" refers to that portion of the tool, or component thereof which is further from the user while the term "proximal" refers to that portion of the tool or component thereof which is closer to the user. While the use of the access assembly is often described herein as engaging an incision, it should be recognized that this is merely exemplary and is not intended to limit the use of the assembly in any way, but rather it should be recognized that the present disclosure is intended to be useable in all instances in situations in which the access assembly engages an incision, a naturally occurring orifice, or any other suitable opening.

Figure 1:
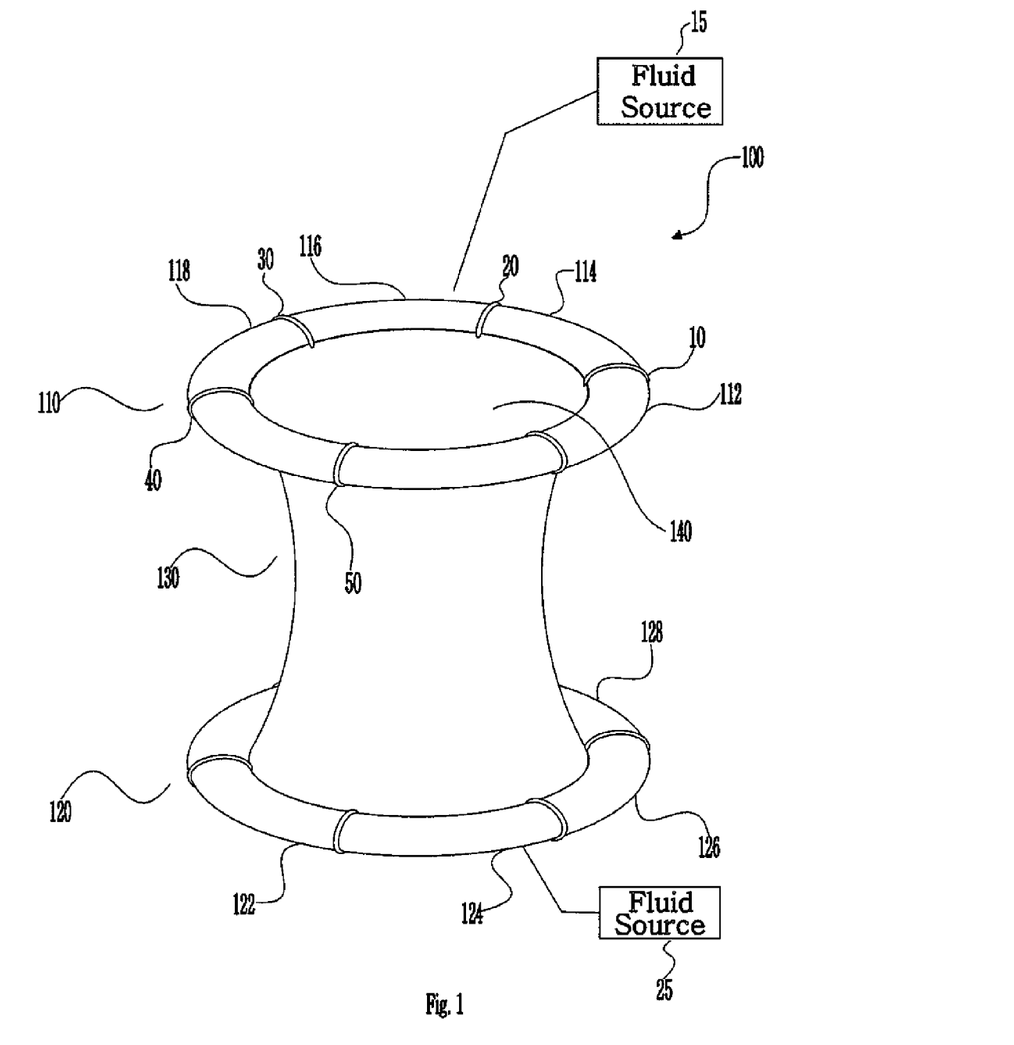
FIG. 1 is a perspective view of an access assembly according to an aspect of the present disclosure, where the top and bottom segmented rings are expanded.

Referring initially to FIG. 1, an assembly for access to a body cavity is shown generally as access assembly 100. Access assembly 100 is configured to be inserted through an incision or other opening in tissue without excessive handling or manipulation of assembly 100 and without a separate insertion device.

Access assembly 100 includes a first ring 110 (or top ring) and a second ring 120 (or bottom ring). A tubular member 130 having a proximal end and a distal end is positioned between the first ring 110 and the second ring 120. The first ring 110 is secured at the proximal end of the tubular member 130, whereas the second ring 120 is secured at the distal end of the tubular member 130. Access assembly 100 may include a cavity or opening 140 for receiving one or more surgical instruments.

In FIG. 1, the first ring 110 is separated into a plurality of adjoining segments. For example, the first ring 110 may include segments 112, 114, 116, 118. Each of the segments may be an expandable segment. The segments may be independently expandable with respect to each other. Similarly, the second ring 120 is separated into a plurality of adjoining segments. For example, the second ring 120 may include segments 122, 124, 126, 128. Each of the segments may be an expandable segment. The segments may be independently expandable with respect to each other. Additionally, each segment 112, 114, 116, 118 may be separated from the other segments by one or more walls 10, 20, 30, 40, 50.

Figure 2:
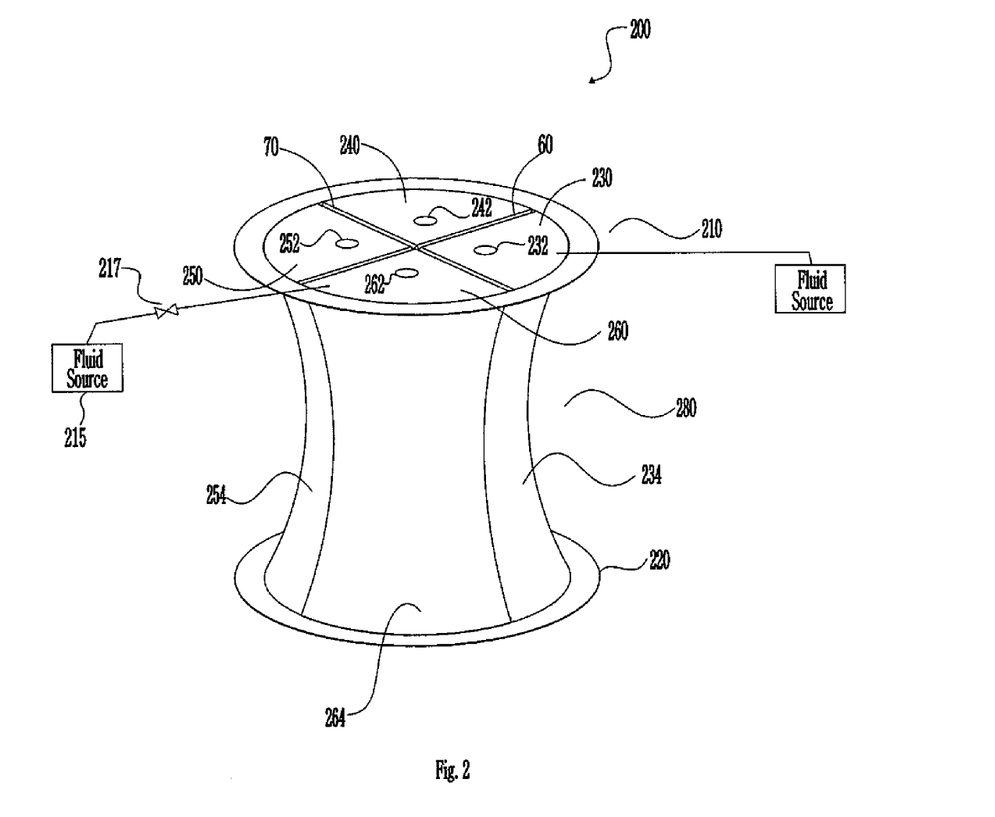
FIG. 2 is a perspective view of an access assembly according to an aspect of the present disclosure, where four sections within the tubular member are expanded.

The first ring 110 and the second ring 120 may be expandable via fluid sources 15, 25, respectively. Therefore, access assembly 100 is configured for operable connection to one or more fluid sources. FIG. 1 illustrates the rings being constructed as separate and distinct, expandable segmented portions. FIG. 2 illustrates the tubular member including expandable sections therein, as described below.

Referring to FIG. 2, a perspective view of an access assembly according to an aspect of the present disclosure, where four sections within the tubular member are expanded is presented.

Access assembly 200 includes a first ring 210 (or top ring) and a second ring 220 (or bottom ring). A tubular member 280 having a proximal end and a distal end is positioned between the first ring 210 and the second ring 220. The first ring 210 is secured at the proximal end of the tubular member 280, whereas the second ring 220 is secured at the distal end of the tubular member 280.

In FIG. 2, the interior portion of the tubular member 280 is separated into a plurality of adjoining or adjacent sections. For example, the interior portion of the tubular member 280 may include sections 230, 240, 250, 260. Each of the sections may be an expandable section. The sections may be independently expandable with respect to each other. In FIG. 2 separate and distinct sections are presented. Additionally, each section 230, 240, 250, 260 may be separated from the other sections by one or more walls 60, 70. However, one skilled in the art may contemplate using a number of different sections in a plurality of different shapes and sizes (see FIGS. 3 and 4). The sections 230, 240, 250, 260 may be expanded or inflated via a fluid source 205. Therefore, access assembly 200 is configured for operable connection to a fluid source 205. One skilled in the art may contemplate using a plurality of fluid sources. Moreover, one skilled in the art may contemplate connecting a fluid source 215 via a valved manifold 217 to a section, for example, section 260. Valved manifolds may be used to connect any fluid source to any expandable/contractable segments or sections presented herein.

Additionally, in FIG. 2, each of the sections 230, 240, 250, 260 includes at least one channel. For example, first section 230 includes channel 232, second section 240 includes channel 242, third section 250 includes channel 252, and fourth section 260 includes channel 262. Each section may extend the entire length of the tubular member 280 from the top ring 210 to the bottom ring 220. For example, the first section 230 includes portion 234 extending from the top ring 210 to the bottom ring 220. Similarly, portion 254 relates to the third section 250 and portion 264 relates to the fourth section 260. Additionally, second portion 240 also includes a portion (not visible) extending the entire length of the tubular member 280.

It is also envisioned that separate expansion devices may be used to expand the segments of the rings 210, 220, and the sections 230, 240, 250, 260 of the interior of the tubular member 280. However, it is also contemplated that one expansion device may be configured to expand segments of the rings 210, 220 and the sections 230, 240, 250, 260 of the interior of the tubular member 280 simultaneously or in different timed intervals via a plurality of different connection mechanisms.

Figure 3:
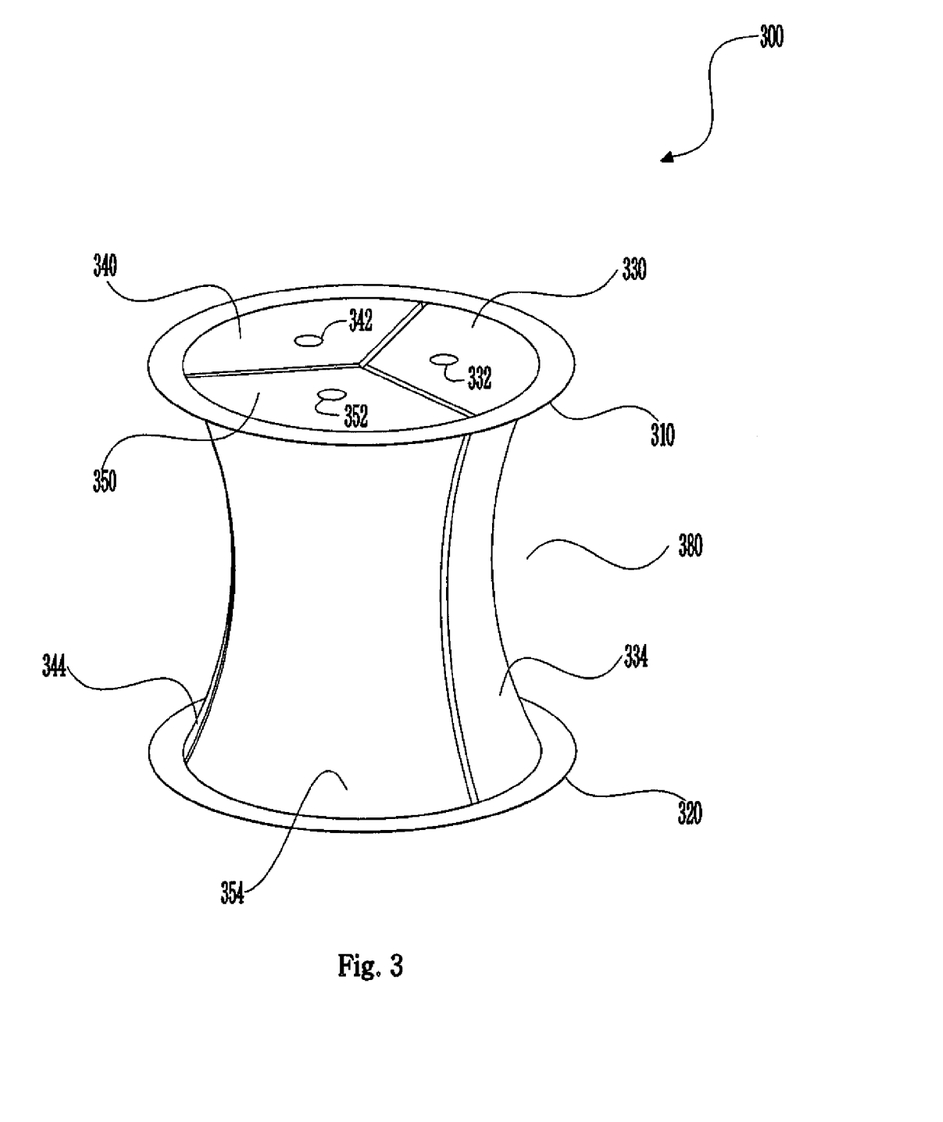
FIG. 3 is a perspective view of an access assembly according to an aspect of the present disclosure, where three sections within the tubular member are expanded.
Figure 4:
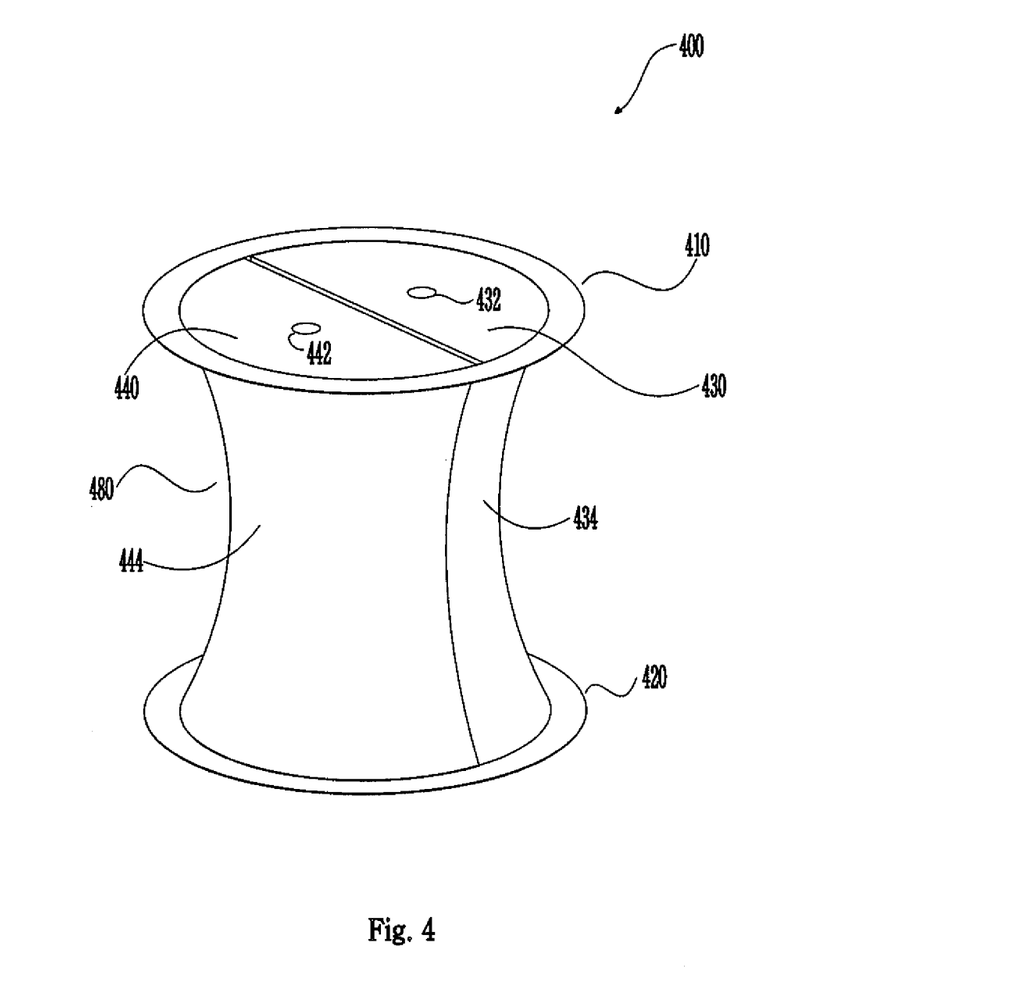
FIG. 4 is a perspective view of an access assembly according to an aspect of the present disclosure, where two sections within the tubular member are expanded.

With reference to FIG. 3, a perspective view of an access assembly according to an aspect of the present disclosure, where three sections within the tubular member are expanded is presented. With reference to FIG. 4, a perspective view of an access assembly according to an aspect of the present disclosure, where two sections within the tubular member are expanded is presented.

Access assembly 300 includes a first ring 310 and a second ring 320. In contrast to FIG. 2, three sections are included within the tubular member 380. The first section 330 includes at least one channel 332 that extends across portion 334 from the top ring 310 to the bottom ring 320. The second section 340 includes at least one channel 342 that extends across portion 344 from the top ring 310 to the bottom ring 320. The third section 350 includes at least one channel 352 that extends across portion 354 from the top ring 310 to the bottom ring 320.

Access assembly 400 includes a first ring 410 and a second ring 420. In contrast to FIGS. 2 and 3, two sections are included within the tubular member 480. The first section 430 includes at least one channel 432 that extends across portion 434 from the top ring 410 to the bottom ring 420. The second section 440 includes at least one channel 442 that extends across portion 444 from the top ring 410 to the bottom ring 420.

Of course, one skilled in the art may contemplate using a number of different sections within the tubular members 380, 480. Each section may include a plurality of channels positioned within or extending through each section. Additionally, it is not necessary that the sections extend the entire length of the tubular members 380, 480. It is contemplated that the sections extend only a portion of the tubular members 380, 480.

Figure 5:
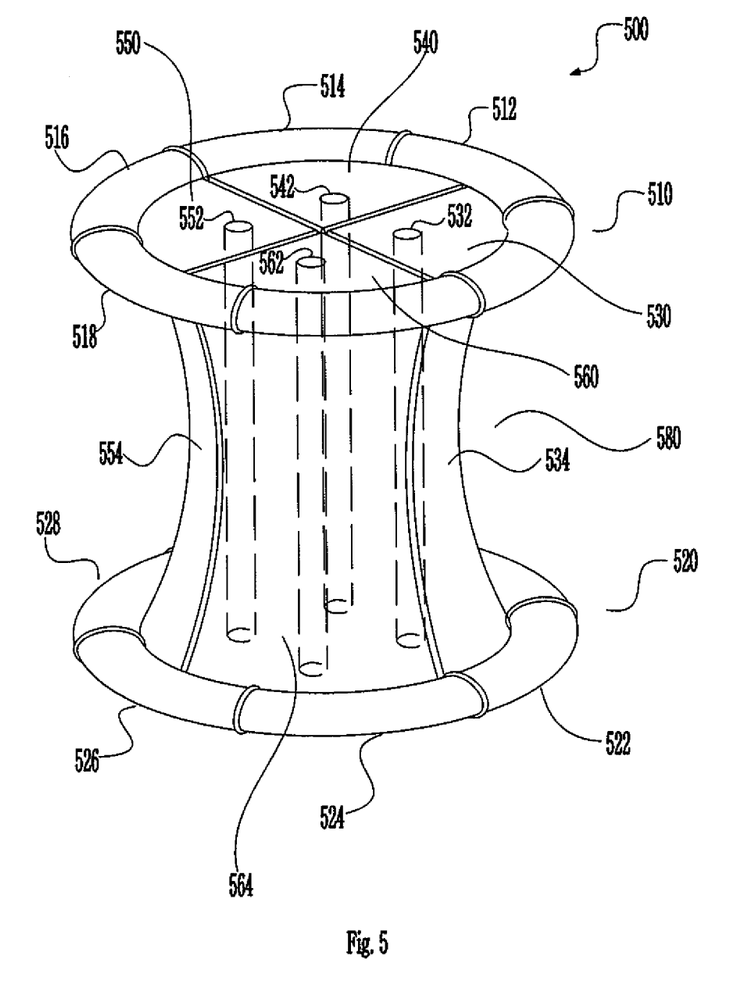
FIG. 5 is a perspective view of an access assembly according to an aspect of the present disclosure, where four sections within the tubular member and the segmented rings are expanded.

With reference to FIG. 5, a perspective view of an access assembly according to an aspect of the present disclosure, where four sections within the tubular member and the segmented rings are expanded is presented.

Access assembly 500 includes a first ring 510 (or top ring) and a second ring 520 (or bottom ring). A tubular member 580 having a proximal end and a distal end is positioned between the first ring 510 and the second ring 520. The first ring 510 is secured at the proximal end of the tubular member 580, whereas the second ring 520 is secured at the distal end of the tubular member 580.

In FIG. 5, the interior portion of the tubular member 580 is separated into a plurality of adjoining or adjacent sections. For example, the interior portion of the tubular member 580 may include sections 530, 540, 550, 560. Each of the sections may be an expandable section. The sections may be independently expandable with respect to each other. Additionally, the first ring 510 is separated into a plurality of segments 512, 514, 516, 518 and the second ring 520 is separated into a plurality of segments 522, 524, 526, 528. Therefore, both rings 510, 520 and the sections 530, 540, 550, 560 of the access assembly 500 are expandable. The segments of the rings 510, 520 may be expanded independently of the sections 530, 540, 550, 560 located within the tubular member 580.

Thus, it is envisioned that separate fluid sources may be used to expand the segments of the rings 510, 520, and the sections 530, 540, 550, 560 of the interior of the tubular member 580. However, it is also contemplated that one fluid may be configured to expand segments of the rings 510, 520 and the sections 530, 540, 550, 560 of the interior of the tubular member 580 simultaneously or in different timed intervals via a plurality of different connection mechanisms. Additionally, each segment 512, 514, 516, 518 of the first ring 510 may be independently expanded relative to each other and each segment 522, 524, 526, 528 of the second ring 520 may be independently expanded relative to each other. It is also noted that each section 530, 540, 550, 560 may be independently expanded relative to each other. The segments and sections may be contracted or expanded at will, as will be described below with reference to FIGS. 6-8.

Referring back to FIG. 5, the access assembly 500 may be an abdominal access system that uses a number of expanded segments and sections to allow sealed access to operate inside an abdominal cavity. The sections 530, 540, 550, 560 may be expanded independently or jointly with varied pressures, as applied by the surgeon. Each section 530, 540, 550, 560 may include at least one channel that allows for at least the passage of surgical instruments. For example, the first section 530 includes a first channel 532 extending the length of the tubular member 580 (shown as portion 534). The second section 540 includes a second channel 542 extending the length of the tubular member 580. The third section 550 includes a third channel 552 extending the length of the tubular member 580 (shown as portion 554). The fourth section 560 includes a fourth channel 562 extending the length of the tubular member 580 (shown as portion 564). The channels 532, 542, 552, 562 are shown as phantom lines extending the entire length of the tubular member 580. The channels 532, 542, 552, 562 may be sealed from losing insufflation gas when a surgical instrument is not present by the fluid pressure used to expand the respective segments 530, 540, 550, 560. That is, in the absence of a surgical instrument, the fluid pressure closes the channel, which may be reopened upon insertion of a surgical instrument.

Therefore, in the expanded configuration, access assembly 500 creates a seal within an opening or channel 532, 542, 552, 562 to prevent the escape of insufflation gas therethrough. Expanded access assembly 500 may be expanded with any suitable fluid, including an insufflation gas or water. Expanded access assembly 500 may define a substantially hourglass shape when viewed from the side. First ring 510 and second ring 520 aid in minimizing movement of the expanded access assembly 500 longitudinally through an opening. Tubular member 580 is of a length sufficient that the first ring 510 is maintained external the body while the second ring 520 is received within the abdominal cavity.

Expandable access assembly 500 may be constructed of plastic, polymer, fabric or other suitable material. Expandable access assembly 500 may be molded, extruded, sewn or formed in any other suitable manner. In one embodiment, the first ring 510 and the second ring 520 may be securely affixed to tubular member 580 by adhesive, bonding, welding or other suitable means. In an alternative embodiment, the first ring 510 and the second ring 520 may be configured for selective engagement with tubular member 580.

In an alternative embodiment, access assembly 500 may include a plurality of openings or channels or lumens. For example, sections 530, 540, 550, 560 may include a plurality of lumens extending at least a portion of an internal length of the tubular member 580. Moreover, although shown including a centrally located opening for each section 530, 540, 550, 560, it is envisioned that the arrangement of access assembly 500 and the one or more plurality of lumens may be modified to better suit an application or procedure. For example, at least one lumen of the plurality of lumens may be configured to directly seal one or more instruments inserted therethrough. Alternatively, each of the plurality of lumens may include one or more valve members (not shown) for receiving an instrument therethrough in a sealing manner. Additionally, the one or more valve members may seal each of the plurality of lumens in the absence of an instrument received therethrough.

Figure 6:
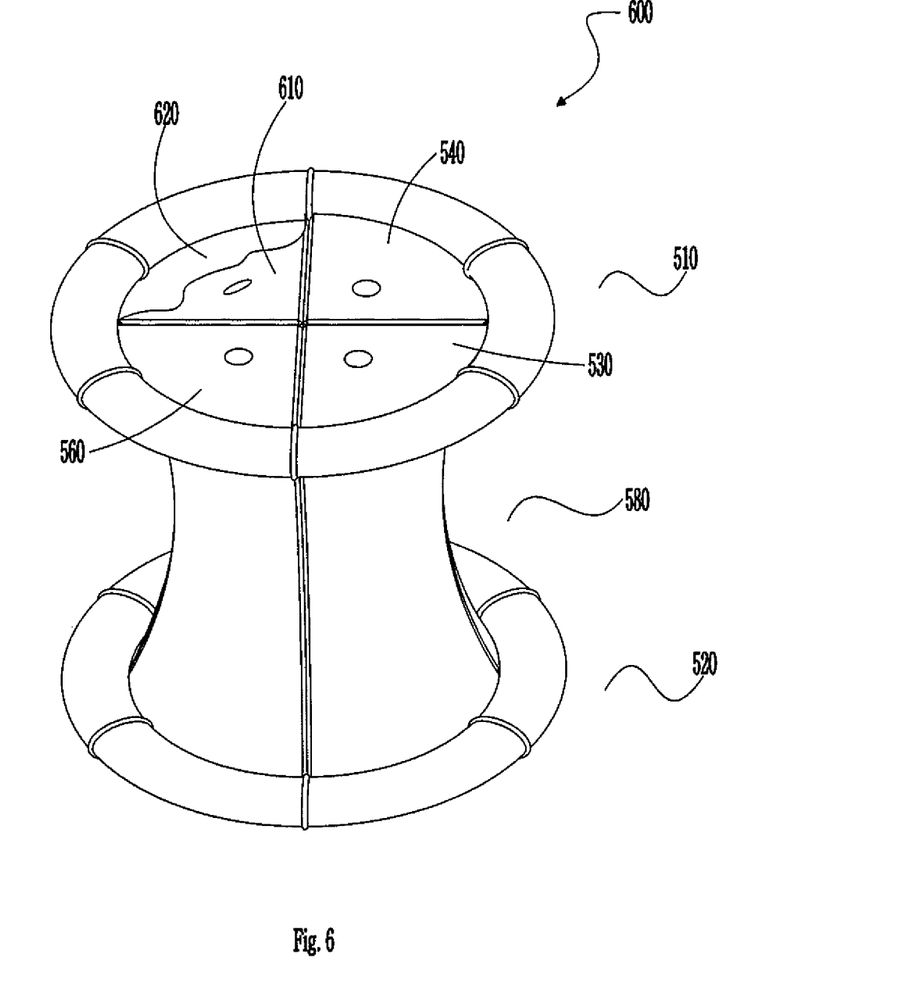
FIG. 6 is a perspective view of an access assembly according to an aspect of the present disclosure, where one section within the tubular member is unexpanded.

With reference to FIG. 6, a perspective view of an access assembly 600 according to an aspect of the present disclosure, where one section within the tubular member is unexpanded is presented.

Like reference numerals of FIG. 6 that identify identical or substantially similar parts of FIG. 5 will not be described in this section. In FIG. 6, the interior portion of the tubular member 580 is separated into a plurality of adjoining or adjacent sections and is positioned between first ring 510 and second ring 520. For example, the interior portion of the tubular member 580 may include sections 610, 530, 540, 560. Each of the sections may be an expandable section. The sections may be independently expandable with respect to each other. As shown in this example embodiment, section 610 has been contracted by the surgeon. Section 610 may have been contracted in order to remove a large specimen through opening 620.

Therefore, if a large specimen is to be removed from the cavity, one or more sections may be strategically contracted in order to allow removal of such specimen by creating a larger opening 620. Additionally, the segments 610, 530, 540, 560 allow the protection of the site of the wound from cell seeding during instrument/specimen exchange. Moreover, one or more sections may be strategically contracted to allow introduction of larger instruments through opening 620.

One skilled in the art may contemplate expanding/contracting any of the sections 610, 530, 540, 560. Such sections may be fully contracted or partially contracted based on the surgeon's determinations of how big or how small a specimen may be. Thus, the surgeon has the capability to select any sections 610, 530, 540, 560 for expansion/contraction.

Figure 7:
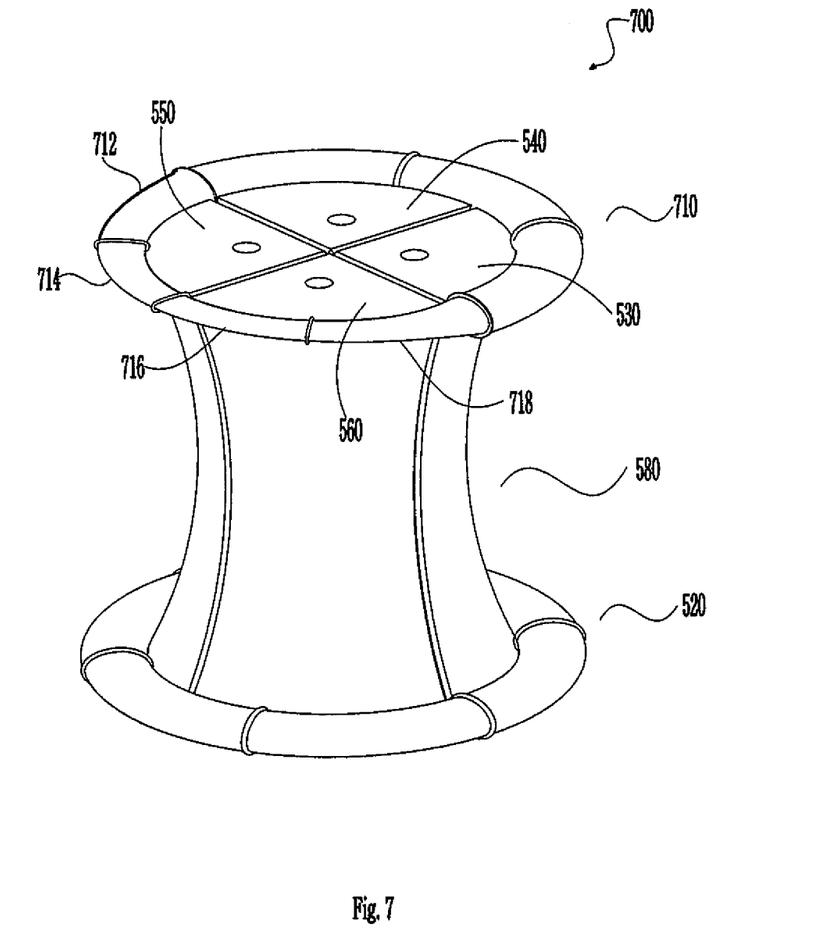
FIG. 7 is a perspective view of an access assembly according to an aspect of the present disclosure, where segments of the top ring are unexpanded.

With reference to FIG. 7, a perspective view 700 of an access assembly according to an aspect of the present disclosure, where segments of the top ring are contracted is presented.

Like reference numerals of FIG. 7 that identify identical or substantially similar parts of FIGS. 5 and 6 will not be described in this section. In FIG. 7, the interior portion of the tubular member 580 is separated into a plurality of adjoining or adjacent sections and is positioned between first ring 710 and second ring 520. For example, the interior portion of the tubular member 580 may include sections 530, 540, 550, 560. Each of the sections may be an expandable section. The sections may be independently expandable with respect to each other. As shown in this example embodiment, segments 712, 714, 716, 718 of the first ring 710 have been contracted by the surgeon. Segments 712, 714, 716, 718 may have been contracted in order to remove a large specimen through one of the openings or channels 552, 562 (see FIG. 5). Thus, the surgeon has the capability to independently or jointly expand or contract segments 712, 714, 716, 718.

Figure 8:
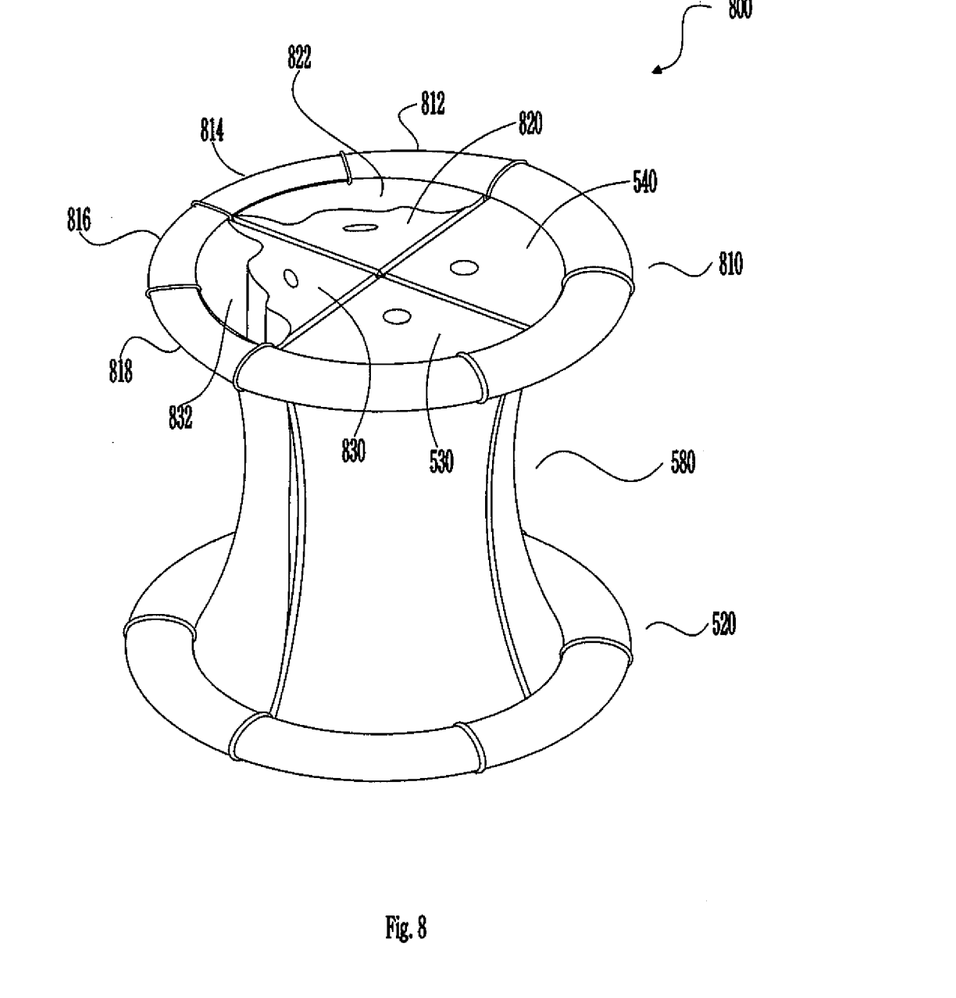
FIG. 8 is a perspective view of an access assembly according to an aspect of the present disclosure, where segments of the top ring are unexpanded and where two sections within the tubular member are unexpanded.

With reference to FIG. 8, a perspective view 800 of an access assembly according to an aspect of the present disclosure, where segments of the top ring are contracted and where two sections within the tubular member are contracted is presented.

Like reference numerals of FIG. 8 that identify identical or substantially similar parts of FIGS. 5-7 will not be described in this section. In FIG. 8, the interior portion of the tubular member 580 is separated into a plurality of adjoining or adjacent sections and is positioned between first ring 810 and second ring 520. For example, the interior portion of the tubular member 580 may include sections 530, 540, 820, 830. Each of the sections may be an expandable section. The sections may be independently expandable with respect to each other. As shown in this example embodiment, sections 820, 830 have been contracted by the surgeon. Additionally, segments 812, 814, 816, 818 of the first ring 810 have been contracted. Sections 820, 830 may have been contracted in order to remove one or more large specimens through openings 822, 832, respectively. Segments 812, 814, 816, 818 may have been contracted in order to remove one or more large specimens through one of the openings or channels 552, 562 (see FIG. 5). Thus, the surgeon has the capability to independently or jointly expand or contract either/or segments 812, 814, 816, 818 and/or sections 530, 540, 820, 830.

Therefore, if a large specimen is to be removed from the cavity, one or more sections and/or segments may be strategically contracted or expanded in order to allow removal of such specimen by creating larger and/or smaller openings. Additionally, the segments 530, 540, 820, 830 allow the protection of the site of the wound from cell seeding during instrument/specimen exchange.

In summary, at least one advantage of the example embodiments of the present disclosure is that an integrated abdominal access system is created for allowing multiple instruments to be used through one incision site, while maintaining insufflation and allowing for large specimen removal through the access assembly.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. An access assembly comprising:
   a tubular member having a proximal end and a distal end, the tubular member including a plurality of sections and a longitudinal axis extending along an entire length of the tubular member from the proximal end to the distal end;
   a first ring constructed as a plurality of adjoining first segments along a first plane and secured at the proximal end of the tubular member; and
   a second ring constructed as a plurality of adjoining second segments along a second plane and secured at the distal end of the tubular member, the second plane being different than the first plane;

wherein each of the plurality of adjoining first segments is independently expandable with respect to the others of the plurality of adjoining first segments;

wherein the first plane extends through each of the plurality of adjoining first segments, the second plane extends through each of the plurality of adjoining second segments, such that the first and second planes are substantially perpendicular to the longitudinal axis;

wherein each of the plurality of sections of the tubular member (i) is configured for operable connection directly with a respective fluid source and (ii) includes one or more channels for receiving one or more surgical instruments therethrough;

wherein each of the plurality of sections of the tubular member is independently expandable via the respective fluid source connected thereto, and each of the plurality of sections and their respective one or more channels extend the entire length of the tubular member from the proximal end to the distal end; and wherein the plurality of sections includes three or more sections arranged in a circular configuration about the longitudinal axis within the tubular member.

2. The access assembly according to claim 1, wherein each of the plurality of adjoining second segments is independently expandable with respect to the others of the plurality of adjoining second segments.

3. The access assembly according to claim 2, wherein each of the plurality of adjoining first segments is independently expandable with respect to each of the plurality of adjoining second segments.

4. The access assembly according to claim 1, wherein the tubular member is configured to be tapered in a first configuration to facilitate insertion through tissue and is configured to define a substantially hour-glass shape in a second configuration.

5. The access assembly according to claim 1, wherein the first and second rings are configured for operable connection with the fluid source such that each of the plurality of adjoining first segments and each of the plurality of adjoining second segments are independently or jointly expanded or contracted.

6. The access assembly according to claim 1, wherein each of the plurality of adjoining first segments is configured to be selectively expanded or contracted to different sizes with respect to the others of the plurality of adjoining first segments and each of the plurality of adjoining second segments is configured to be selectively expanded or contracted to different sizes with respect to the others of the plurality of adjoining second segments.

7. The access assembly according to claim 1, wherein each of the plurality of sections of the tubular member is configured to be selectively expanded or contracted to different sizes.

8. The access assembly according to claim 1, wherein a first pressure is applied to the plurality of adjoining first segments to expand the plurality of adjoining first segments to a first size and a second pressure is applied to the plurality of adjoining second segments to expand the plurality of adjoining second segments to a second size, the first size being larger than the second size.

9. The access assembly according to claim 1, wherein the one or more channels of each of the plurality of sections is sealed from losing an insufflation gas when a subject inserts and removes the one or more surgical instruments from the one or more channels.

10. A method of accessing a body cavity, the method comprising:

providing a tubular member having a proximal end and a distal end, the tubular member including a plurality of sections and a longitudinal axis extending along an entire length of the tubular member from the proximal end to the distal end;

constructing a first ring as a plurality of adjoining first segments along a first plane, the first ring secured at the proximal end of the tubular member;

constructing a second ring as a plurality of adjoining second segments along a second plane, the second ring secured at the distal end of the tubular member, and the second plane being different than the first plane; and independently expanding each of the plurality of adjoining first segments with respect to each other;

wherein the first plane extends through each of the plurality of adjoining first segments, the second plane extends through each of the plurality of adjoining second segments, such that the first and second planes are substantially perpendicular to the longitudinal axis;

wherein each of the plurality of sections of sections of the tubular member (i) is configured for operable connection directly with a respective fluid source and (ii) includes one or more channels for receiving one or more surgical instruments therethrough;

wherein each of the plurality of sections of the tubular member is independently expandable via the respective fluid source connected thereto, and each of the plurality of sections and their respective one or more channels extend the entire length of the tubular member from the proximal end to the distal end; and wherein the plurality of sections includes three or more sections arranged in a circular configuration about the longitudinal axis within the tubular member.

11. The method according to claim 10, further comprising operably connecting the first and second rings with the fluid source such that each of the plurality of adjoining first and second segments is independently or jointly expanded or contracted.

12. The method according to claim 10, further comprising selectively expanding or contracting each of the plurality of adjoining first segments to different sizes with respect to the others of the plurality of adjoining first segments and selectively expanding or contracting each of the plurality of adjoining second segments to different sizes with respect to the others of the plurality of adjoining second segments.

13. The method according to claim 10, further comprising selectively expanding or contracting the plurality of sections of the tubular member to different sizes.

14. The method according to claim 10, wherein the one or more channels of each of the plurality of sections is sealed from losing an insufflation gas when a subject inserts and removes the one or more surgical instruments from the one or more channels.

15. A method of accessing a body cavity, the method comprising:

providing a tubular member having a plurality of sections, the tubular member being configured to be tapered in a first configuration to facilitate insertion through tissue and being configured to define a substantially hour-glass shape in a second configuration, and having a longitudinal axis extending along an entire length of the tubular member from a proximal end to a distal end;

constructing a first ring to have a plurality of adjoining first segments along a first plane, the first ring secured at the proximal end of the tubular member; constructing a second ring to have a plurality of adjoining second segments along a second plane, the second ring secured at the distal end of the tubular member, the second plane being different than the first plane;

inserting the tapered access assembly through tissue;

adjusting the access assembly in the second configuration; and independently expanding each of the plurality of adjoining first segments with respect to each other;

wherein the first plane extends through each of the plurality of adjoining first segments, the second plane extends through each of the plurality of adjoining second segments, such that the first and second planes are substantially perpendicular to the longitudinal axis;

wherein each of the plurality of sections of the tubular member (i) is configured for operable connection directly with a respective fluid source and (ii) includes one or more channels for receiving one or more surgical instruments therethrough;

wherein each of the plurality of sections of the tubular member is independently expandable via the respective fluid source connected thereto, and each of the plurality of sections and their respective one or more channels extend the entire length of the tubular member from the proximal end to the distal end; and wherein the plurality of sections includes three or more sections arranged in a circular configuration about the longitudinal axis within the tubular member.

16. The method according to claim 15, further comprising operably connecting each of the plurality of adjoining first segments of the first ring and each of the plurality of adjoining second segments of the second ring to a different fluid source such that each of the plurality of adjoining first segments and each of the plurality of adjoining second segments are selectively expanded or contracted into a plurality of different sizes.

* * * * *